(12) United States Patent
Spenciner

(10) Patent No.: US 9,474,521 B2
(45) Date of Patent: Oct. 25, 2016

(54) SYSTEMS, DEVICES, AND METHODS FOR EXTRUDING A SUTURE CORE

(71) Applicant: Medos International Sàrl, Le Locle (CH)

(72) Inventor: David B. Spenciner, North Attleboro, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 179 days.

(21) Appl. No.: 14/229,474

(22) Filed: Mar. 28, 2014

(65) Prior Publication Data

US 2015/0272568 A1   Oct. 1, 2015

(51) Int. Cl.
*A61B 17/04* (2006.01)
*A61B 17/295* (2006.01)
*A61B 17/29* (2006.01)

(52) U.S. Cl.
CPC ....... *A61B 17/0467* (2013.01); *A61B 17/0483* (2013.01); *A61B 17/295* (2013.01); *A61B 2017/2925* (2013.01)

(58) Field of Classification Search
CPC .......... A61B 17/0467; A61B 17/0483; A61B 17/0485; A61B 17/0401; A61B 17/06166; A61B 17/0618; A61B 2017/2926; A61B 17/282; A61B 17/30; A61B 17/29; A61B 17/32; A61B 17/12009; A61B 2017/12018; A61B 17/0469; A61B 17/06061; A61B 17/28; A51B 2017/0411; A51B 2017/06185
USPC ........................................ 606/151, 144, 148
See application file for complete search history.

(56) References Cited

U.S. PATENT DOCUMENTS

| | | | |
|---|---|---|---|
| 5,643,289 A | 7/1997 | Sauer et al. | |
| 5,846,254 A * | 12/1998 | Schulze | A61B 17/0469 289/1.2 |
| 5,875,792 A | 3/1999 | Campbell, Jr. et al. | |
| 5,906,629 A | 5/1999 | Oren et al. | |
| 6,249,631 B1 | 6/2001 | LeVey et al. | |
| 6,786,913 B1 * | 9/2004 | Sancoff | A61B 17/0469 606/146 |
| D523,554 S | 6/2006 | Weisel | |
| 7,131,980 B1 | 11/2006 | Field et al. | |
| 7,377,926 B2 | 5/2008 | Topper et al. | |
| 7,381,212 B2 | 6/2008 | Topper et al. | |
| 7,817,891 B2 | 10/2010 | Lavenne et al. | |

(Continued)

OTHER PUBLICATIONS

International Search Report for Application No. PCT/US2015/019379, mailed May 21, 2015 (6 pages).

*Primary Examiner* — David C Eastwood
*Assistant Examiner* — Mikail Mannan

(57) ABSTRACT

Systems, devices, and methods for cutting a filament or suture having an extrudable inner core member are provided. In one exemplary embodiment, a device includes a compression element to compress an inner core away from a knot disposed at a distal end of the suture, and a cutting element disposed within a portion of the compression element to cut the inner core after it has been compressed. As a result, an amount of extrudable inner core that extends distally beyond the knot is minimized without negatively impacting the integrity of the knot. In other embodiments, the compression and cutting elements are separately provided as two different devices. The actions of compressing and cutting can be performed using a variety of techniques, including those known to those skilled in the art. Methods for clamping the inner core and then cutting a portion of the inner core are also provided.

14 Claims, 10 Drawing Sheets

(56) References Cited

U.S. PATENT DOCUMENTS

| | | |
|---|---|---|
| 7,879,046 B2 | 2/2011 | Weinert et al. |
| 2005/0192633 A1 | 9/2005 | Montpetit |
| 2006/0161183 A1* | 7/2006 | Sauer ................ A61B 17/0467 606/148 |
| 2008/0281355 A1* | 11/2008 | Mayer .................... A61L 17/00 606/228 |
| 2012/0289975 A1 | 11/2012 | Martin et al. |

* cited by examiner

SYSTEMS, DEVICES, AND METHODS FOR EXTRUDING A SUTURE CORE

FIELD

The present disclosure relates to systems, devices, and methods for managing filament or suture having an extrudable core, and more particularly relates to controlling an amount of the extrudable core that extends from a distal end of the filament or suture.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. While a variety of different techniques and devices can be used for ligament or tendon attachment, filament or suture, also referred to herein as a joining element, is often used to help secure the ligament or tendon to bone.

Despite the fact that the joining element has been used in connection with ligament and tendon repairs for quite some time, there is still a risk of failure resulting from the joining element coming loose, for instance due to load application. Loads that are exerted on the joining element between bone and tendon are very different. Over long periods of time it can be desirable for the joining element to contract such that the joining element tensions between the bone and tendon. Meanwhile, movements on the part of the patient may subject the joining element to rapidly increasing high loads, under which the connection can sometimes fail.

Some embodiments of joining elements include a more solid outer sleeve with a flexible, extrudable core disposed within at least a portion of the outer sleeve. Knots can be formed on either or both ends of the outer sleeve, for instance by forming a knot in the flexible, extrudable core, and the core can extend distally beyond the knots, and thus distally beyond the terminal ends of the outer sleeve. Over time, the joining element can be hydrated by fluids in the body. This can cause a length of the outer sleeve to shrink, while the flexible core can actually expand in length due to the core being configured to absorb fluid. For example, the core can include silicone and salt, and the salt can help absorb fluid surrounding the joining element, in turn causing terminal ends of the core to grow further away from the knots at the distal ends of the outer sleeve. A person skilled in the art may find it beneficial to limit the amount of silicone that extends from the knots at the distal ends of the outer sleeve.

Accordingly, there is a need for devices, systems, and methods to reduce the amount of flexible material disposed distally beyond a knot associated with a joining element having an extrudable core.

SUMMARY

Systems, devices, and methods are generally provided for managing an extrudable core of a filament or suture. In one exemplary embodiment, a device for cutting a suture having an extrudable core includes a compression element, a cutting element, and a handle assembly. The compression element can have a first jaw and a second jaw pivotally coupled thereto, the jaws being configured to engage therebetween a suture having an extrudable core and configured to close to compress the extrudable core away from a knot associated with the suture. The cutting element can be configured to pass through the first jaw to cut a suture having an extrudable core that is disposed between the first and second jaws after the jaws have been closed. A handle assembly can be operable to first actuate the compression element to close the jaws and subsequently to actuate the cutting element to cut a suture having an extrudable core that is disposed between the closed first and second jaws.

The first and second jaws can be configured to apply a force gradient that is greater at a distal end of the jaws than at a proximal end of the jaws. In some embodiments, a face of the second jaw can be angularly disposed with respect to a face of the first jaw when the jaws are in a closed position. A closed position can be, for example, a position at which the jaws compress an extrudable core away from a knot associated with a suture that is disposed between the first and second jaws. An angle formed between the face of the first jaw and the face of the second jaw in the closed position can be in the range of about 0.5 degrees to about 20 degrees.

The device can be used in conjunction with a suture, the suture including an outer sleeve, an extrudable core disposed within the outer sleeve, and a knot formed proximate to a terminal end of the outer sleeve. The extrudable core can be configured to extend on a first side of the knot, within the outer sleeve, and on a second, laterally opposed side of the knot, past a terminal end of the outer sleeve. In some embodiments, the knot can be formed by the extrudable core. The first and second jaws can be configured to engage a portion of the extrudable core that is disposed on the second, laterally opposed side of the knot.

One exemplary embodiment of a system for cutting a suture having an extrudable core can include a compression instrument and a cutting instrument. The compression instrument can have a first jaw and a second jaw pivotally coupled thereto, and a trigger operable to close the first and second jaws around a suture having an extrudable core and squeeze at least a portion of the core away from a knot associated with the suture. The cutting instrument can be configured to cut a suture having an extrudable core after at least a portion of the core has been squeezed away from a knot associated with the suture by the first and second jaws.

The first and second jaws can be configured to apply a force gradient that is greater at a distal end of the jaws than at a proximal end of the jaws. In some embodiments, a face of the second jaw can be angularly disposed with respect to a face of the first jaw when the jaws are in a closed position. A closed position can be, for example, a position at which the jaws squeeze at least a portion of an extrudable core away from a knot associated with a suture disposed between the first and second jaws. An angle formed between the face of the first jaw and the face of the second jaw in the closed position can be in the range of about 0.5 degrees to about 20 degrees.

In some embodiments, the compression instrument and the cutting instrument can be integrally formed such that the cutting instrument passes through the second jaw of the compression instrument to cut a suture having an extrudable core around which the first and second jaws are closed. In at least some of such embodiments, the trigger can be operable to advance the cutting instrument through a suture having an extrudable core around which the first and second jaws are closed to cut the suture. The trigger can, for example, be configured to advance a first distance to close the first and second jaws of the compression instrument, and a second distance to operate the cutting instrument to cut the suture.

The second distance can extend further than an end point of the first distance. Alternatively, the trigger can be configured to advance a first distance to close the first and second jaws of the compression instrument, and it can subsequently cause a gear to operate the cutting instrument to cut the suture. In still other embodiments, the compression instrument and the cutting instrument can be separate instruments. In such embodiments, the cutting instrument can have its own trigger to operate the cutting instrument to cut a suture having an extrudable core around which the first and second jaws of the compression instrument are closed.

The system can be used in conjunction with a suture, the suture including an outer sleeve, an extrudable core disposed within the outer sleeve, and a knot formed proximate to a terminal end of the outer sleeve. The extrudable core can be configured to extend on a first side of the knot, within the outer sleeve, and on a second, laterally opposed side of the knot, past a terminal end of the outer sleeve. In some embodiments, the knot can be formed by the extrudable core. The first and second jaws of the compression instrument can be configured to close around a portion of the extrudable core that is disposed on the second, laterally opposed side of the knot.

One exemplary embodiment of a surgical method can include implanting a suture having an extrudable core and a knot associated therewith within a patient, the extrudable core being disposed on opposed lateral sides of the knot. The method can further include clamping a portion of the extrudable core disposed on one side of the knot to advance the extrudable core a distance away from the knot. Still further, the method can include cutting a portion of the extrudable core that was advanced a distance away from the knot by the clamping step such that the cut portion is no longer associated with a remaining portion of the extrudable core.

In some embodiments, the steps of clamping and cutting can be performed by a single instrument having a housing with both a clamping element a cutting element associated therewith. In such embodiments, the instrument can include a trigger. The method can then include advancing the trigger a first distance to clamp and advance the extrudable core, and advancing the trigger a second distance to cut a portion of the extrudable core that was advanced during clamping. The second distance can extend further than an end point of the first distance. Alternatively, the method can include advancing the trigger a first distance to clamp and advance the extrudable core, and subsequently operating the trigger to actuate a gear that initiates cutting a portion of the extrudable core that was advanced during clamping. In some other embodiments, the steps of clamping and cutting can be performed by two separate instruments, each operable independently from the other.

The step of clamping a portion of the extrudable core can further include engaging a portion of the extrudable core disposed adjacent to the knot with first and second jaws prior to engaging a portion of the extrudable cored disposed further from the knot with the first and second jaws. In some embodiments, the method can also include removing from the patient the cut portion of the extrudable core.

BRIEF DESCRIPTION OF DRAWINGS

This invention will be more fully understood from the following detailed description taken in conjunction with the accompanying drawings, in which.

DETAILED DESCRIPTION

Figure 1A:
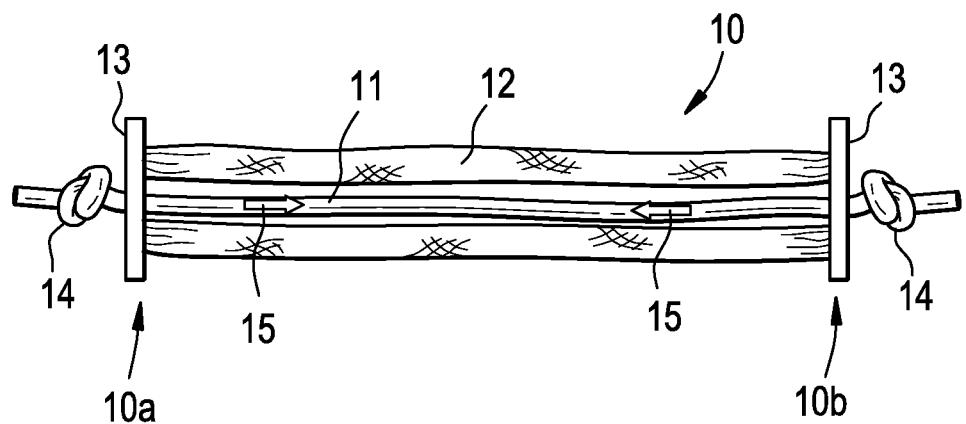
FIG. 1A is a schematic view of one exemplary embodiment of part of a suture having an extrudable core shortly after a test use in vitro or in vivo, i.e., after an implantation.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In the present disclosure, like-numbered components of the embodiments generally have similar features and/or purposes. Further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the size and shape of the components with which the systems and devices are being used, the anatomy of the patient, and the methods and procedures in which the systems and devices will be used. The figures provided herein are not necessarily to scale. Additionally, a number of terms may be used throughout the disclosure interchangeably but will be understood by a person skilled in the art. By way of non-limiting example, the terms "joining element," "suture," and "filament," and the terms "portion," "element," and "instrument" when referring to a compression or cutting portion, element, or instrument may be used interchangeably.

Devices, systems, and methods are generally provided for managing joining elements, e.g., sutures and filaments, that include an extrudable core. The core can be extrudable because it can be of a flexible nature and capable of being displaced with respect to an outer sleeve of the joining element. The disclosures herein are designed to minimize an amount of extrudable material that is exposed at a distal end of the joining element without negatively impacting the integrity of the joining element. For example, in at least some of the embodiments provided for herein, a knot can be disposed at a distal end of the joining element, and thus as the extrudable core is managed, at least a portion of the extrudable core can be left to extend distally beyond the knot so that the integrity of the knot is not harmed. The disclosures provided for herein generally include a compression element or instrument to help move the extrudable core away from a knot, and a cutting element or instrument configured to cut away at least a portion of the extrudable core that is moved away from the knot. In some embodiments, the compression element or instrument and the cutting element or instrument are part of the same device, while in other embodiments they are two separate devices.

Joining Elements

Figure 1B:
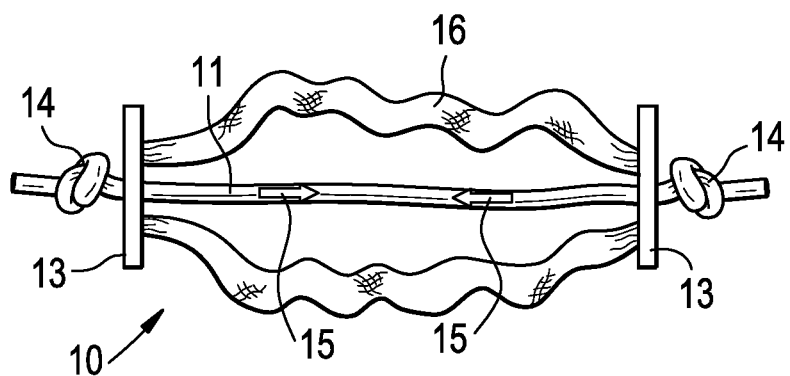
FIG. 1B is a schematic view of part of the suture of FIG. 1A after a longer period of time since the start of said use.

Two schematic, exemplary embodiments of a part 10, 10' of a joining element for use with the devices, systems, and methods provided for herein are illustrated in FIGS. 1A-1B and 2A-2B. FIGS. 1A-1B illustrate a part 10 of a joining element or suture having an outer sleeve or jacket 12, sometimes referred to as a sheath, with a pre-tensioned, extrudable core 11 disposed therein. A joining construction, for example a mesh 13, can optionally be disposed at each end 10a, 10b of the part 10, and woven with terminal ends of the jacket 12. The core 11 can be routed through the mesh 13 and formed into a knot 14. Thus, as shown, the core 11 can extend from a first side 14a of the knot 14, toward and into the jacket 12, and it can also extend from a second, laterally opposed side 14b of the knot 14, distally away from the knot 14 and jacket 12. In other embodiments, there is no such mesh 13, and thus the part 10 of the joining element includes the jacket 12 and the pre-tensioned, extrudable core 11 with no additional material associated with ends 10a, 10b of the part 10. Unless otherwise noted, the term distal as used herein with respect to a joining element generally reflects movement away from a knot and an outer sleeve, and thus typically away from a patient, even if that means that such movement is towards a user.

The sheath or jacket 12 can be composed of a rigid material, which can be compressed under the effect of chemical and physical processes that take place over the course of time, as known to those skilled in the art. In some embodiments, the rigid material can be thread. The resulting force that can trigger the aforementioned compression process can be the force resulting from pre-tensioning the core minus the tension force acting on the thread from the environment (for example, the tensioning force applied during stitching). As the tensioning force exerted on the thread by the environment decreases, the resulting compressive force acting on the jacket can increase. This, in turn, can favor the compression of the jacket, resulting in an accelerated contraction of the thread or of the textile structure formed from the latter. This can result in tensioning of the thread or of the textile structure until an equilibrium is once again established between the forces described above, or the jacket is able to support the compressive force acting on it, without slow compression.

The material for the jacket can be characterized in that it permits controlled plastic deformations over a defined period of time, i.e., the material can have a distinct yield point and can behave substantially elastically below the yield point. This can mean that the main component of the material can have a glass transition temperature above body temperature or should have a high crystallinity and additionally can have a high degree of fracture toughness. Typical representatives of this class of materials can include, for example, blends or copolymers of structural polymers with a glass transition temperature ($T_g$) distinctly above body temperature and polymers with a $T_g$ distinctly below 0° C. (blend: polylactides with trimethylene carbonates, copolymer: polyhydroxybutyrate with polyhydroxyvalerate). However, this function can also be performed by highly crystalline polymers such as polyethylene (PE), polyamides, or polyesters, in which case the structure of the envelope can be provided with defined yield points, for example by local thinning of the cross section, incorporation of reinforcements and kinks, or local periodic variation of the modulus of elasticity by variation of the polymer orientation. In some embodiments, the jacket 12 can be composed in particular of a mesh, for example of threads arranged helically around an inner core. The threads can be braided or otherwise interlaced, and selected from a group of degradable and nondegradable polymers typically used in filament and suture formation, including but not limited to stretched polyesters, polyamides, polyolefins, polyaramides, expanded or densely halogenated polymers, and high-strength ladder polymers such as polyetherether ketone and captones. In other embodiments the jacket 12 can be formed from a continuous, monofilament.

The core 11 can be composed of a flexible material. As a result, it can be considered extrudable, that is to say that it can be moved to different locations by applying pressure to it. In some embodiments, the configuration that results from applied pressure can remain even after the pressure is no longer applied. Examples of materials for the core are preferably materials of an elastomeric nature and with minimal tendency to creep, typical representatives of which are cross-linked polymers such as silicones or polyurethanes, which can also be composed of degradable components if complete degradation of the thread is sought. In some embodiments, the core 11 can be a swellable material. A person skilled in the art will recognize a number of swellable materials suitable for use in joining elements, but in some instances it can include osmotically active substances (e.g., salt, particulate form of a water-soluble substance such as saccharides) to attract fluid like water. In the rest position, the core 11 can be shorter than the distance between the opposed meshes 13, such that the inserted core 11 in the view of FIG. 1A is pre-tensioned. This is indicated by the arrows 15. When the jacket 12 is rigid, the meshes 13 can be kept spaced apart despite the effect of the spring tension of the core 11.

FIG. 1B illustrates the development of a part 10 of the joining element over a long period of time, for example over several weeks. After a period of time, possibly interrupted by forces of the short-lasting type mentioned above, the jacket 12 can deform, designated in the figure as a changed jacket 16. By means of the pre-tensioning effect of the core 11, the meshes 13 can move toward one another, and the band made up of the parts 10 of the joining elements can contract. This can result in a change in length of up to approximately 80 percent from the original length.

In many instances, multiple parts 10 of joining elements as provided for herein can be coupled together to form a structure for use in a medical treatment. For example, multiple parts 10 of joining elements can be used as a suture material for wound treatment or as a wide band. In some such instances, many joining elements can be arranged alongside one another and in succession to form a band that can be processed. The joining elements can be advantageously surrounded in their entirety by an envelope with controlled kinking behavior. However, it may also be possible for each individual element to be surrounded by such an envelope, particularly if the whole construction is to be as flexible and formable as possible. If a large force quickly builds up on such a band and abates again after a certain time, for example a force that builds up in tenths of seconds, possibly lasts for a few seconds and then returns to zero, the jacket 12 then holds the individual parts 10 in position and thus also the band and, consequently, the organ, tissue, etc. connected thereto, for example a tendon and a bone.

A person skilled in the art will recognize that the functions of the core and jacket as described herein can also be interchanged, i.e., before processing the jacket can be pre-tensioned and the core can be acted on by pressure. Further, it is also possible for the pre-tensioning to be applied only after the processing (for example after the stitching in the case of the thread).

Figure 2A:
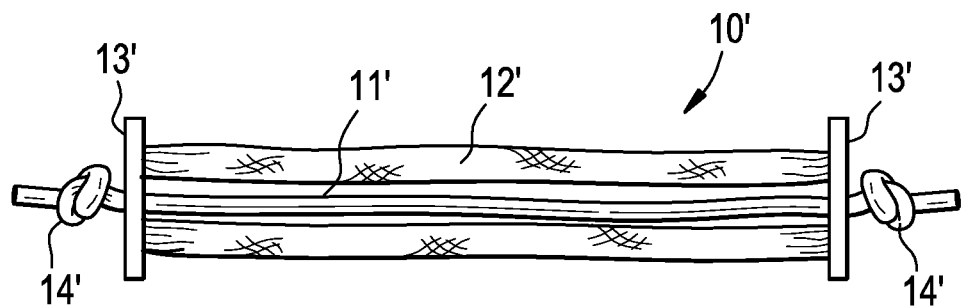
FIG. 2A is a schematic view of another exemplary embodiment of part of a suture having an extrudable core shortly after a test use in vitro or in vivo, i.e., after an implantation.
Figure 2B:
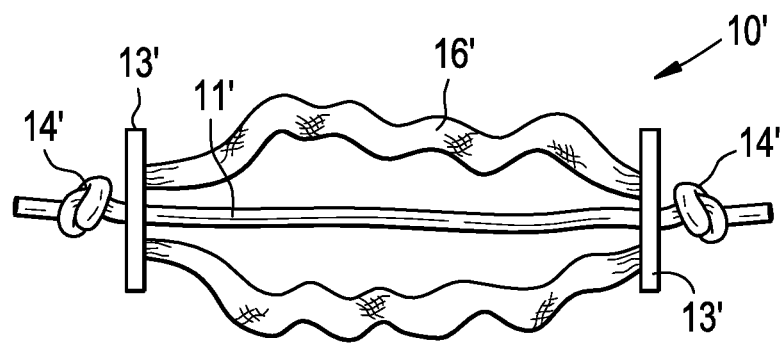
FIG. 2B is a schematic view of part of the suture of FIG. 2A after a longer period of time since the start of said use.

FIGS. 2A-2B illustrate another embodiment of a part 10' of a joining element or suture having an outer filament or jacket 12' with a pre-tensioned, extrudable core 11' disposed therein. In the illustrated embodiment, the jacket 12' can structurally decompose, for example by at least the partial use of the aforementioned biodegradable polymers. Accordingly, at least part of the material can initially lose some of its modulus of elasticity, and thus its stability against kinking, as a result of the uptake of water and the incipient hydrolysis of the incorporated biodegradable polymers. However, at the same time the jacket 12' can gain in terms of its plastic deformation capacity. As the degradation proceeds, this can result in a loss of mass and physical breakdown. This is illustrated by a comparison of FIG. 2A at the start of use to FIG. 2B after a longer period of time.

The part 10' of a joining element is provided with a jacket 12', which can lose its structural integrity over the course of time. This can be seen from the thinner jacket 16' in FIG. 2B. The degrading jacket 16' can offer less resistance to the flexible core 11', and the distance between the joining constructions, as shown meshes 13', can become shorter. If, however, rapid tensile or impact forces act on the joining element part 10' during this process, then it can again react rigidly because the stiffness properties of the jacket 12' may not in principle have been changed by the deformation, particularly in relation to its resistance against rapid stressing. The stiffness properties of the jacket 12' may not be macroscopically different (departing from the only schematic representation in the figure), and may have only become weaker relative to the core 11'. This can involve in particular the elastic properties of the jacket material that can be of relevance in short-term stressing.

A person skilled in the art will recognize a variety of other configurations of joining elements with which the systems, devices, and methods provided for herein can be used. By way of non-limiting examples, other configurations of an inner core can be used, including inner cores having adjacent molecules (e.g., polymeric macromolecules of known biocompatible polymers) and lubricants that can act as a plasticizer. Examples and further details of the configurations described herein, as well as other joining element configurations, are provided for in U.S. Patent Application Publication No. 2008/0281355 of Mayer et al., the content of which is incorporated by reference herein in its entirety.

Figure 3A:
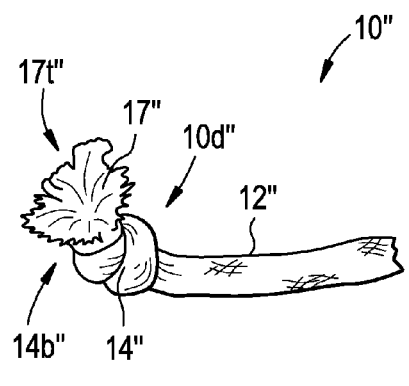
FIG. 3A is a schematic view of a distal end of another embodiment of a suture having an extrudable core, the suture being in a dry configuration.
Figure 4A:
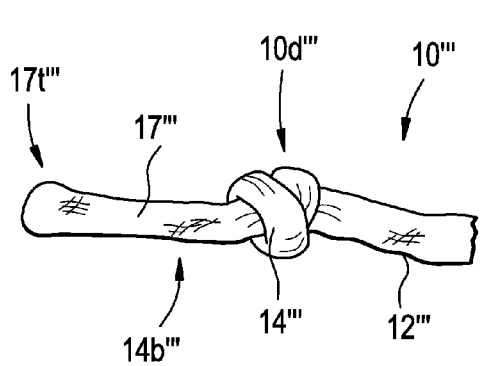
FIG. 4A is a schematic view of a distal end of yet another embodiment of a suture having an extrudable core, the suture being in a dry configuration.

FIGS. 3A-3B and FIGS. 4A-4B illustrate that at cut ends of a joining element 10", 10'", an extrudable core 11", 11'" can have a tendency to extrude beyond an outer sleeve 12", 12'". FIG. 3A illustrates a joining element 10" having an outer sleeve 12" with an extrudable core 11" disposed therein in a pre-hydration or dry configuration. A knot 14" can be formed at a distal end 10d" of the joining element 10", and a tail 17" can extend from a side 14b" of the knot 14" opposite to the remainder of the joining element 10". As shown, a terminal end 17t" of the tail 17" can be frayed as a result of the tail 17" being cut by a general cutting device. FIG. 4A similarly illustrates a joining element 10'" having an outer sleeve 12'" with an extrudable core 11'" disposed therein, a knot 14'" formed at a distal end 10d'" of the joining element 10'", and a tail 17'" extending from a side 14b'" of the knot 14'" opposite to the remainder of the joining element 10'". The tail 17'" is longer than the tail 17", and any fraying thereof can be less prominent due to the longer length of the tail 17'".

Figure 3B:
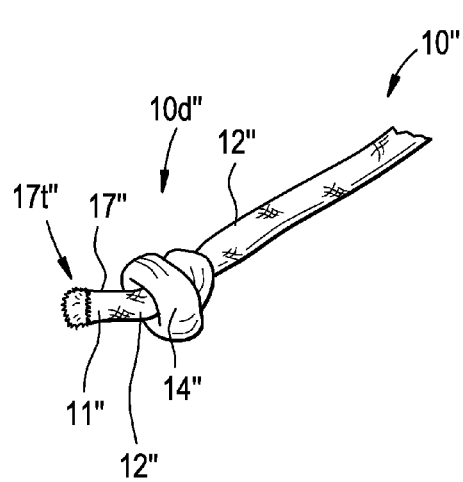
FIG. 3B is a schematic view of the distal end of the suture of FIG. 3A after the suture has been hydrated.
Figure 4B:
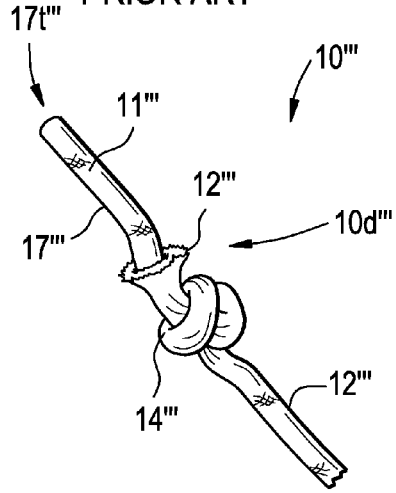
FIG. 4B is a schematic view of the distal end of the suture of FIG. 4A after the suture has been hydrated.

After the joining elements 10", 10'" have been exposed to fluid, such as water, saline, or synovial fluid, for a period of time, the resulting, hydrated configurations are shown in FIGS. 3B and 4B. As shown, the outer sleeves 12", 12'" can retract or shrink such that they are now closer to the knot 14", 14'" than they were in the dry configuration. The extrudable cores 11", 11'", on the other hand, can both extend a distance further away from the knot 14", 14'" than they were in the dry configuration due to materials in the inner core absorbing the fluid. As shown, the cores 11", 11'" extend further distally than the outer sleeves 12", 12'". A terminal end 12t" of the outer sleeve 12" can remain frayed, or become more frayed, and as illustrated a terminal end 12t'" of the outer sleeve 12'" can be more frayed due to the combination of the expanding extrudable core 11'" and the shrinking outer sleeve 12'". As shown in FIGS. 3B and 4B, the terminal end 17t", 17t'" of the tail 17", 17'" can now be the terminal end of the extrudable core 11", 11'", with a large portion of the inner core 11", 11'" now being exposed as the tail or distal end of the joining element 10", 10'".

A person having skill in the art will recognize that having a portion of the joining element extend distally beyond the knot can be helpful to help protect the integrity of the knot. If too little material is disposed distally beyond the knot, the knot can have a tendency to unravel. However, chunks of extrudable cores 11", 11'" of the length illustrated in FIGS. 3B and 4B that are made of materials provided for herein, e.g., silicone, can be less desirable. It is these lengths of extrudable cores extending distally beyond the knots of the joining elements that the systems, devices, and methods provided for herein are designed to manage.

Devices for Managing Joining Elements

Figure 5:
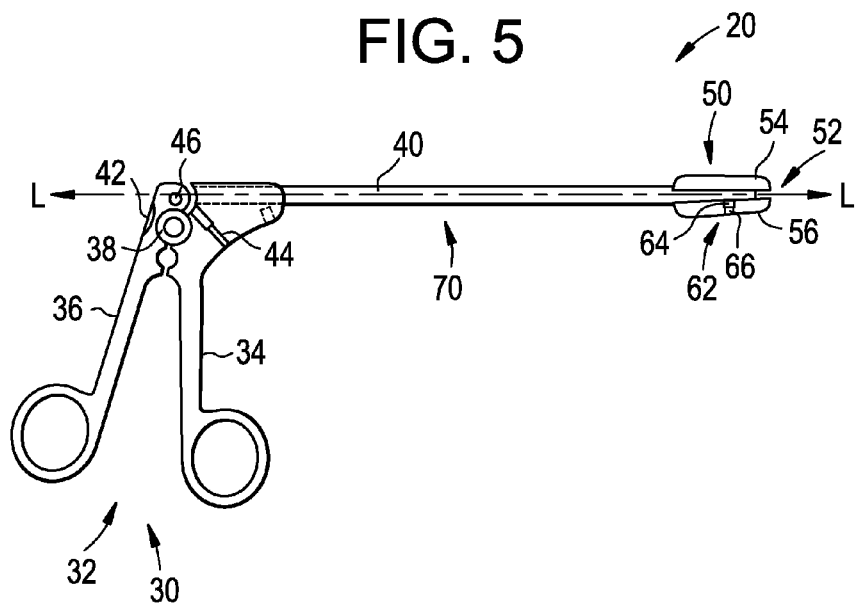
FIG. 5 is a schematic side view of one exemplary embodiment of an instrument for grasping a suture having an extrudable core.

FIG. 5 generally shows an instrument 20 that can be used to help manage joining elements. It generally includes a handle portion or assembly 30 for operating an end effector 50, a shaft 70 linking the handle portion 30 to the end effector 50, and an end effector 50 configured to minimize an amount of extrudable core that extends distally of a knot of a joining element without affecting the integrity of the knot. The end effector 50 can include both a clamping or compression element or instrument 52, as shown first and second jaws 54, 56, and a cutting element instrument 62, as shown a cutting blade 64 associated with an actuation rod 66.

Handle Assemblies

The handle portion 30 can have any type of design known in the art for operating end effectors. In the illustrated embodiment, the handle portion 30 has a scissors-like configuration that includes a trigger 32 having a first handle 34 pivotally mounted to a second handle 36 at a pivot point 38 such that both handles 34, 36 are configured to pivot about the pivot point 38. In other embodiments, one handle can be stationary while the other handle moves towards and away from the stationary handle. Pivotal movement of one handle with respect to the other can actuate the end effector 50. For example, one handle, as shown the first handle 34, can be coupled to an operating rod 40 that extends through the shaft 70, while the second handle 36 can be coupled to the shaft itself 70. Pivotal movement of the first handle 34 towards the second handle 36 can then distally advance the operating rod 40 to actuate the end effector 50.

As described in greater detail below, actuation of the end effector 50 can involve two separate actions. One action can involve operating the compression element 52 to close the jaws 54, 56 around an extrudable core, while the second action can include operating the cutting element 62 to cut the extrudable core disposed between the two jaws 54, 56. In the illustrated embodiment, pivoting the first handle 34 towards the second handle 36 can distally advance the actuating rod 40 along a longitudinal axis L extending through the shaft 70 to cause the jaws 54, 56 to close. A person skilled in the art will recognize a variety of ways by which an actuating rod can cause jaws to close, but in one exemplary embodiment, a distal end of the rod 40 can be configured to apply a compressive force to the second jaw 56 to cause the second jaw 56 to advance toward the first jaw 54. In alternative embodiments, the rod 40 can be configured to apply a compressive force to the first jaw 54 and/or both jaws 54, 56, or it can be configured to effect pivotal movement of the jaws 54, 56 with respect to each other to clamp the extrudable core therebetween. Such a position can sometimes be referred to as a closed or locked position. Further, other types of mechanical and electrical configurations for operating jaws can be incorporated into the device to allow the handle assembly 30 to operate the compression element 52 without departing from the spirit of the present disclosure. By way of non-limiting example, one or more linkages can be included as part of the handle assembly 30 to help translate movement from the handle assembly 30 to the compression element 52.

The second, cutting action can also be actuated by a portion of the handle assembly 30. In the illustrated embodiment, a button 42 is provided that is in communication with the cutting element 62 by a hard wire (not shown). A user who presses the button 42 can send a signal to the cutting element 62, via the hard wire, to cause the cutting element 62 to advance toward the first jaw 54 to cut the extrudable core. For purposes of both safety and accuracy, the button 42 can be configured to only send a signal to cut when the jaws 54, 56 are closed. In alternative embodiments, the actuating rod 40 can also be configured to actuate the cutting element 62. For example, after the actuating rod 40 advances distally to close the jaws 54, 56, the first handle 34 can be further pivoted towards the second handle 36 to continue distal advancement of the actuating rod 40. Such advancement can be designed to advance the cutting element 62 through a portion of the jaws 54, 56 to cut the core disposed between the jaws 54, 56. In still further alternative embodiments, after the actuating rod 40 advances distally to close the jaws 54, 56, the first handle 34 can be further pivoted towards the second handle 36 to cause the rod 40 to advance and engage a gear coupled to the cutting element 62. As the handles 34, 36 are squeezed together, the gear can begin to turn to advance the cutting element 62 through a portion of the jaws 54, 56 to cut the core disposed between the jaws 54, 56. Other ways of communicating actuation between the handle assembly 30 and the cutting element 62 are also possible, including, by way of further non-limiting example, wireless, remote frequency communication between the button 42 and the cutting element 62.

Exemplary features to help control the handles 34, 36 and the end effector 50 can also be incorporated into the design of the handle assembly 30. By way of non-limiting example, an adjustable blocking member 44 can be provided to help control how close the handle portions 34, 36 can get to one another. The adjustable blocking member 44 can be a stop screw disposed in the first handle 34 and configured to move toward the second handle 36 to set a stop position. When the second handle 36 engages the stop screw, no further pivoting of one handle with respect to the other may occur. The adjustable blocking member 44 can be used to help set a desired distance of travel for the jaws 54, 56 because the distance traveled by the handles 34, 36 can correlate to the distance traveled by the jaws 54, 56. In other embodiments, a shear pin 46 can be provided in one of the handles, as shown the second handle 46, to help prevent overloading the jaws 54, 56. For example, the shear pin 46 can be designed to yield at about 60% of the stress which would damage the jaws 54, 56 and/or extrudable core disposed therein.

Figure 6:
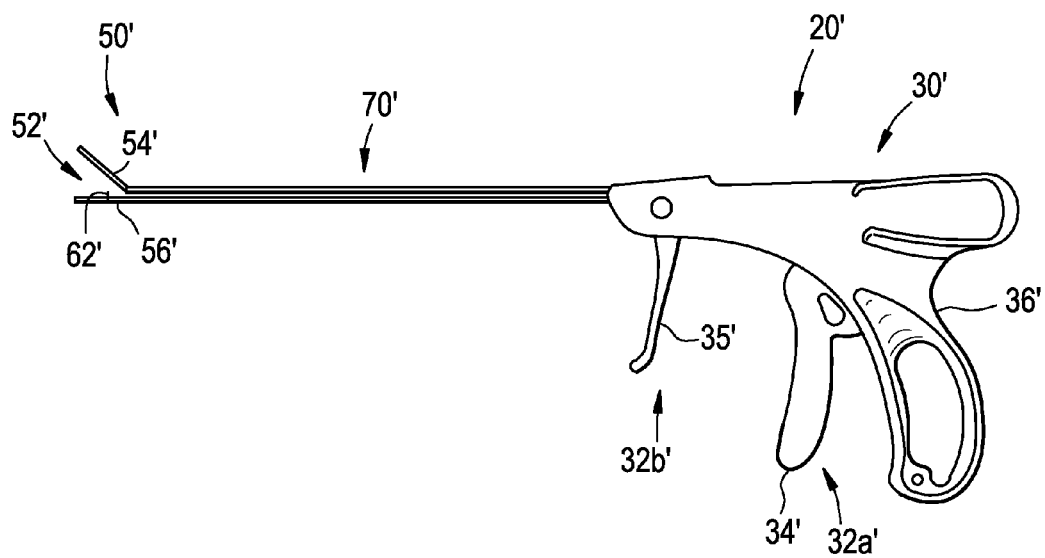
FIG. 6 is a schematic side view of another exemplary embodiment of an instrument for grasping a suture having an extrudable core.

FIGS. 6 and 7A-7D illustrate other non-limiting embodiments of handle portions that can be used in conjunction with the disclosures provided for herein. For example, the device 20' of FIG. 6 illustrates a device having a handle assembly 30' with two triggers 32a', 32b' associated therewith for operating an end effector 50' and a shaft 70' extending between the handle assembly 30' and the end effector 50'. More particularly, a stationary handle 36' can be provided for a user to grip the device 20', and the two triggers 32a', 32b' can be actuated to cause the end effector 50' to perform the compression and cutting steps. As shown, the first trigger 32a' can include an actuation handle 34' configured to pivot with respect to the stationary handle 36' to clamp jaws 54', 56' of a compression element 52' around an extrudable core. This can sometimes be referred to as a closed or locked position. In the illustrated embodiment, the jaws 54', 56' are configured to pivot at a proximal end thereof, thus illustrating an alternative embodiment of an end effector 50'. Further, the second trigger 32b' can include a lever 35' that can be pivoted towards the stationary handle 36' to activate a cutting element 62' associated with the end effector 50' to cut an extrudable core disposed between the jaws 54', 56'. In some embodiments, the cutting element 62' can be prevented from actuating when the jaws 54', 56' are not closed. Once the core is cut, the triggers 32a', 32b' can be returned to their initial position, and thus the compression and cutting elements 52', 62' as well. Just as in other embodiments, mechanisms other than triggers 32a', 32b' and their associated components can also be used to operate the compression element 52' and the cutting element 62'.

Figure 7A:
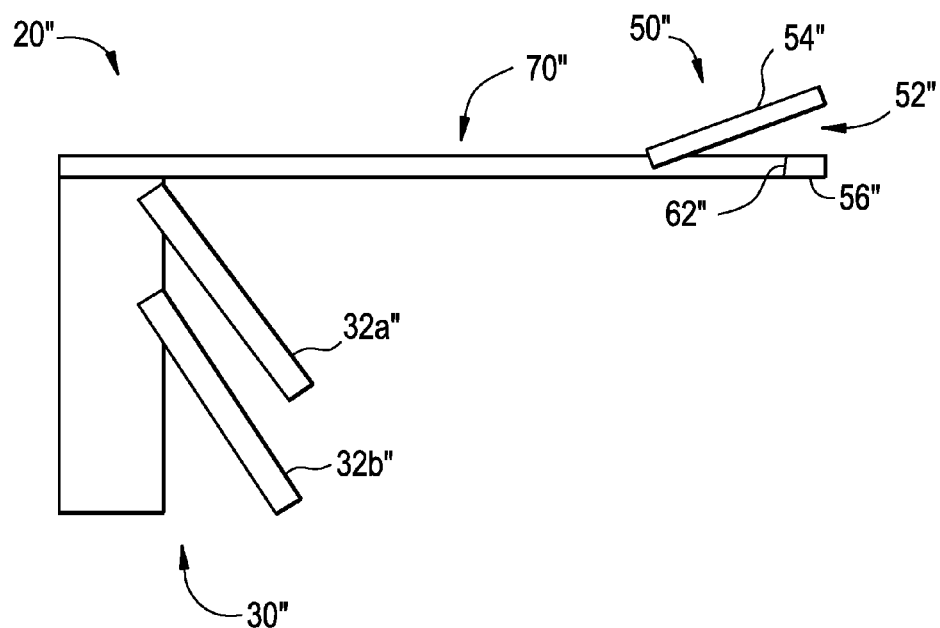
FIG. 7A is a schematic view of one exemplary embodiment of an instrument for grasping and cutting a suture having an extrudable core, first and second triggers of the instrument being in respective first positions in which both a grasping instrument and a cutting instrument are also in respective first positions.

FIGS. 7A-7D provide for schematic illustrations of an instrument 20" having a handle portion 30" with two triggers 32a", 32b", an end effector 50" configured to clamp and cut an extrudable core, and a shaft 70" extending therebetween. As shown in FIG. 7A, a first trigger 32a" and a second trigger 32b" can both be disposed in a first, open position. As a result, first and second jaws 54", 56" of a compression element 52" can also be in a first, open position, and a cutting element 62" can be disposed in the second jaw 56" in a first, pre-cut position.

Figure 7B:
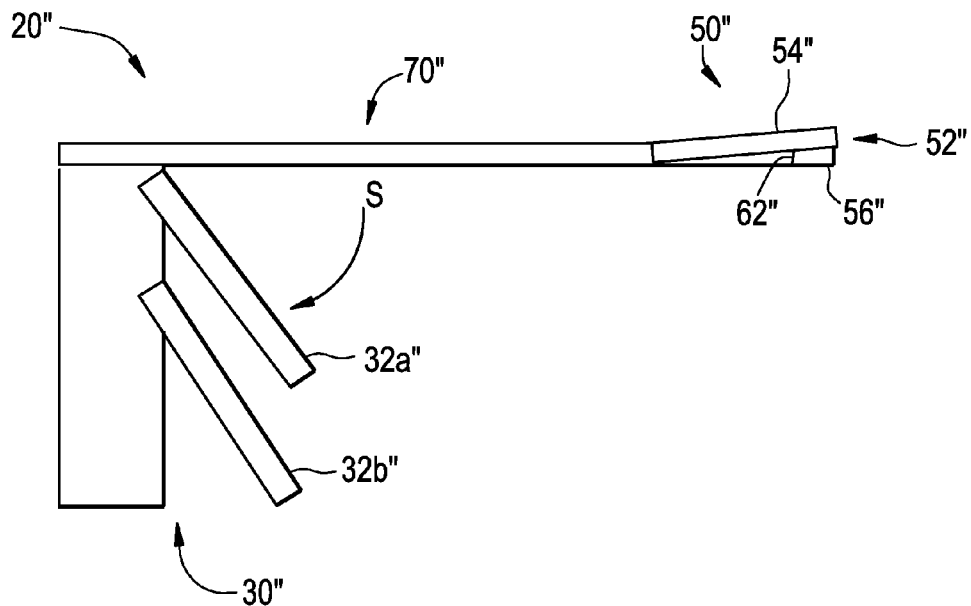
FIG. 7B is a schematic view of the instrument of FIG. 7A, the first trigger being in a second position in which the grasping instrument is in a second position and the second trigger being in the first position in which the cutting instrument remains in the first position.
Figure 7C:
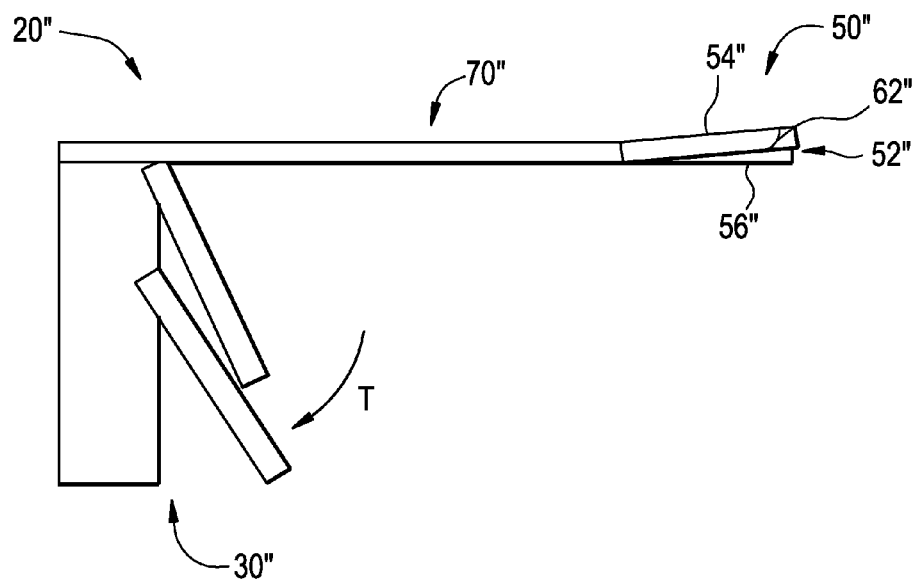
FIG. 7C is a schematic view of the instrument of FIG. 7B, the first and second triggers being in second positions, and thus the grasping instrument and the cutting instrument also being in respective second positions.
Figure 7D:
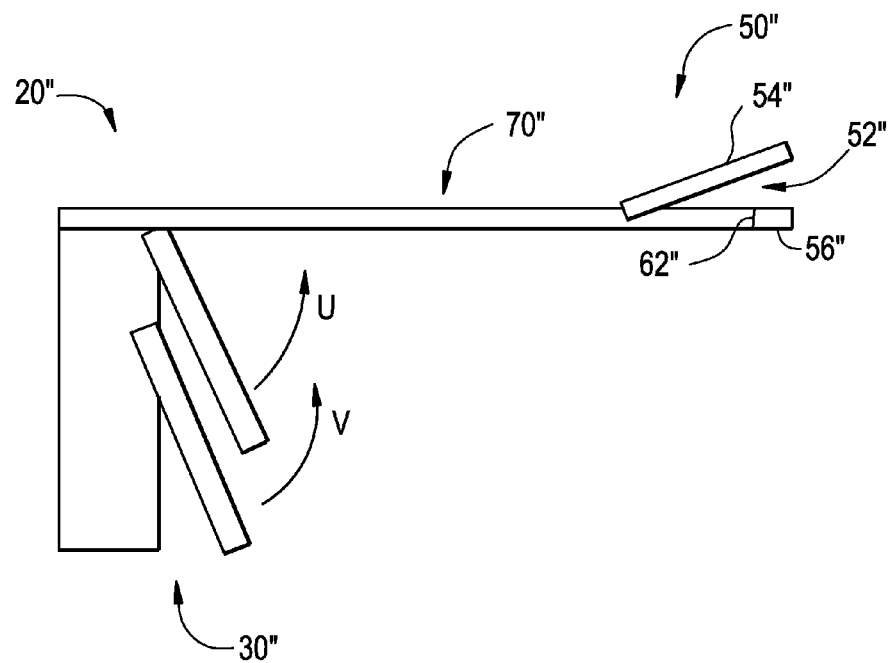
FIG. 7D is a schematic view of the instrument of FIG. 7C, the first and second triggers beginning to move back to their respective first positions so that the grasping instrument and the cutting instrument can also be disposed in their respective first positions.

FIG. 7B shows that the first trigger 32a" can be activated, for instance by rotating it towards a handle portion 36" of the instrument in a direction S, to close or clamp the jaws 54", 56" around an extrudable core disposed therebetween. In the illustrated embodiment, the jaws 54", 56" are configured to pivot with respect to each other, although other configurations can also be used to clamp an extrudable core therebetween. After the core has been clamped, the second trigger 32b" can be activated, for instance by rotating it towards the handle portion 36" in a direction T, to drive the cutting element 62" through the extrudable core and into a portion of the first jaw 54", as shown in FIG. 7C. Once the extrudable core has been cut, both triggers 32a", 32b" can be returned to their original positions, as shown in FIG. 7D by directions U and V, respectively, such that the cutting portion 62" is again disposed in the second jaw 56" in a first, pre-cut position and the first and second jaws 54", 56" are again in their first, open position.

A person skilled in the art will recognize a variety of other ways by which the clamping and cutting actions can be performed by an instrument, including other mechanical, electrical, and electrical-mechanical designs. The actuation of the jaws 54, 56 is by no means limited to the types of disclosures provided for herein. By way of non-limiting examples, other mechanical types of handle assemblies can be used to actuate the jaws 54, 56, and can include features such as a pistol-grip, levers, triggers, and sliders. In some embodiments, various mechanical and electrical components, such as motors, controllers, and levers, can be included as part of a housing of the handle assembly, either disposed therein or extending therefrom. Further, a person skilled in the art will recognize other functions that the handle assembly 30 can perform without departing from the spirit of the present disclosure. Additional information about some of the configurations provided for herein, as well as other types of handle portions and related components that can be used and adapted for use to perform the compression and cutting actions disclosed herein can be found in U.S. Pat. No. 5,906,629 of Oren, U.S. Pat. No. 7,377,926 of Topper et al., U.S. Pat. No. 7,381,212 of Topper et al., U.S. Pat. No. 7,879,046 of Weinert et al., and U.S. Pat. No. D523,554 of Weisel, the content of each which is incorporated by reference herein in its entirety.

Compression Elements and Cutting Elements

FIGS. 8A-8D illustrate one exemplary embodiment of a portion of an end effector 150 that includes both a clamping or compression element 152 and a cutting element 162. More particularly, the clamping element 152 can include first and second jaws 154, 156 that are configured to grasp and compress portions of a joining element 110 disposed therebetween. The joining element 110 can be of a nature described above, and thus can include an extrudable core 111 disposed within an outer sleeve 112 and extending distal of a knot 114, on a second side 114b thereof. In the illustrated embodiment, the jaws 154, 156 are configured to grasp a portion of the sleeve 112 in which the extrudable core 111 is disposed and located distal of the knot 114. When the joining element 110 is disposed in a patient, the portion of the patient's body with which the joining element 110 is disposed can be located on an opposite side 114a of the knot 114.

Figure 8A:
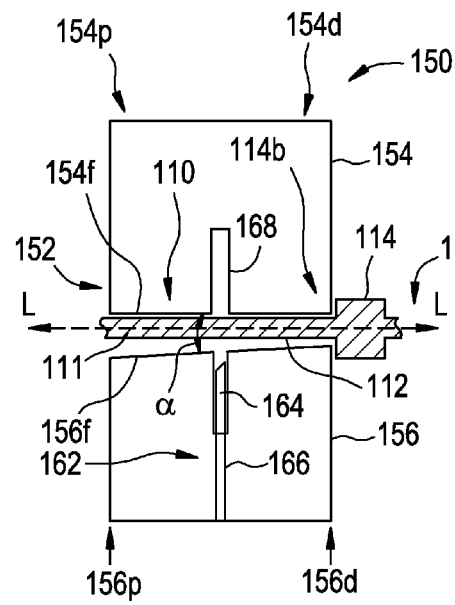
FIG. 8A is a schematic cross-sectional view of one exemplary embodiment of a portion of jaws of an instrument for grasping and cutting a suture having an extrudable core, the jaws being in an open position and a cutting element being disposed in a first position.

As shown in FIG. 8A, faces 154f, 156f of the jaws 154, 156 can be angularly disposed with respect to each other such that they are not parallel to each other. This angular configuration can help to direct and control the movement of the extrudable core 111 by applying a force gradient that is greater at a distal end 154d, 156d of the jaws 154, 156, i.e., close to the knot 114, than at a proximal end 154p, 156p of the jaws 154, 156. Movement of the core 111 can occur with respect to the sleeve 112 such that at least a portion of the outer sleeve 112 has partially filled or unfilled volume. As shown, the face 154f of the first jaw 154 can be substantially parallel to the longitudinal axis L that extends through a shaft (not shown), and thus generally between the jaws 154, 156, of the instrument, while the face 156f of the second jaw 156 can be disposed at an angle with respect to the longitudinal axis L. This forms an angle α between the faces 154f, 156f. The angle α can be in the range of about 0.5 degrees to about 20 degrees, and in one exemplary embodiment the angle α is about 5 degrees. In other embodiments, the faces 154f, 156f can both be parallel with respect to the longitudinal axis L, and thus each other. Still further, in other embodiments, the jaws 154, 156 can be configured to have some degree of flexibility with respect to each other such that they start in a first angled configuration but advance to a second configuration that is either angled or a parallel configuration. For example, an increasing amount of force or pressure can be applied to the jaws to cause one of the jaws 154, 156 to pivot with respect to the other to change the angle α such that the angle α decreases or becomes 0 degrees. In a parallel configuration, the faces 154f, 156f can be approximately parallel to each other. Such a configuration can help to further advance a core away from a knot.

The cutting element 162 can be disposed in one of the jaws, as shown the second jaw 156, and configured to cut through the sleeve 112 and extrudable core 111. In the illustrated embodiment, the cutting element 162 includes a cutting blade 164 that is associated with an actuation rod 166 such that movement of the actuation rod 166 initiated by a handle assembly (not shown) can translate to the cutting blade 164. Such movement allows the cutting blade 164 to travel through the sleeve 112 and extrudable core 111 and into at least a portion of the first jaw 154, where it can be received by a bore 168 formed therein and configured to receive the cutting blade 164. In other embodiments, the cutting element 162 can be disposed adjacent to a terminal end of the jaws 154, 156 such that it can cut the sleeve 112 and/or the core 111 pushed towards it by the jaws 154, 156, and portions of the sleeve 112 and/or core 111 that were cut can be disposed of in a manner known to those skilled in the art. In such an embodiment, with reference to FIG. 8A, the jaws 154, 156 could extend between the knot 114 and the cutting element 162, terminating prior to the cutting element 162, and the cutting element being able to cut the sleeve 112 and/or core 111 that extends distally from the jaws 154, 156, i.e., away from the knot 114.

Shapes and sizes of the jaws 154, 156, and the components associated therewith, such as the actuation rod 166, cutting blade 164, and receiving bore 168, can depend, at least in part, on the configurations of these components and the other components of the device, the configuration of the joining element 110, the sleeve 112, and extrudable core 111, and the type of procedure with which the instrument is being used. In one exemplary embodiment, the jaws 154, 156 are made of metal, such as a surgical grade stainless steel, or a polymer, and the cutting blade can be made of a metal, such as Nitinol. In other embodiments, the jaws 154, 156 and cutting blade 164 can be made from similar materials, and/or one portion of the jaws 154, 156 or its related components can be made from different materials than other portions. Further, a variety of features can be incorporated into the jaws 154, 156 to assist in grasping extrudable core therein. By way of non-limiting example, one or more grooves can be formed in the faces 154f, 156f of the jaws 154, 156 to help grasp the sleeve 112 and core 111.

Figure 8B:
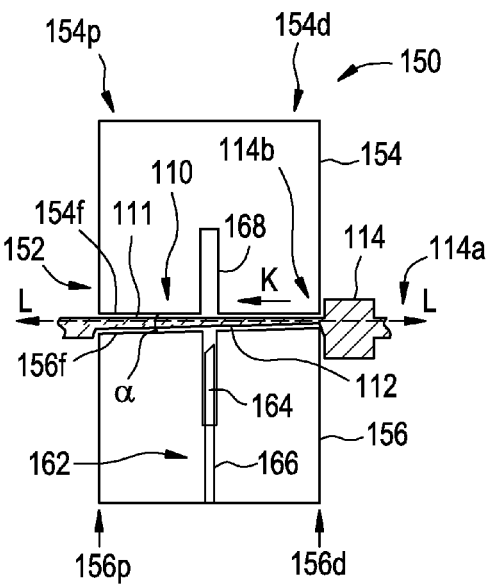
FIG. 8B is a schematic cross-sectional view of the portion of jaws of the instrument of FIG. 8A, the jaws being in a closed position and the cutting element being disposed in a first position.

In use, a handle assembly can be operated to close the jaws 154, 156. In the illustrated embodiment, the second jaw 156 advances towards the first jaw 154 in response to actuation of a handle assembly to place the first and second jaws 154, 156 into a closed configuration in which the jaws 154, 156 engage the sleeve 112, and thus the extrudable core 111 disposed therein. As shown in FIG. 8B, because of the angular orientation of the face 156f, the distal ends 154d, 156d of the jaws 154, 156 first engage the sleeve 112 and extrudable core 111 and squeeze or otherwise compress the core 111 away from the knot 114, in a direction K, towards the more open end of the angled configuration. After the jaws 154, 156 have moved into the closed configuration and the extrudable core 111 has been displaced away from the knot 114 as desired, the handle assembly can be operated to actuate the cutting element 162.

Figure 8C:
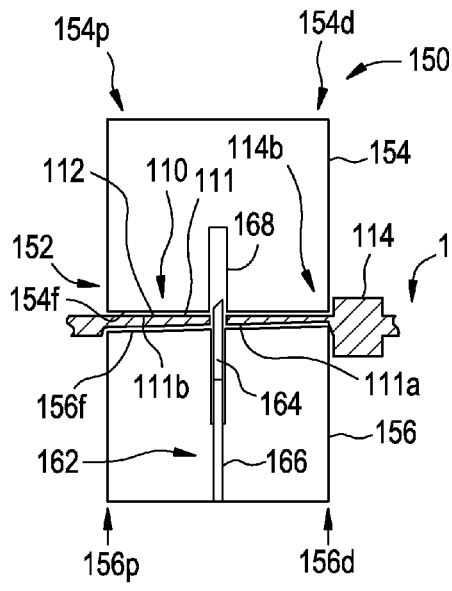
FIG. 8C is a schematic cross-sectional view of the portion of jaws of the instrument of FIG. 8B, the jaws being in a closed position and the cutting element being disposed in a second position.

As shown in FIG. 8C, the cutting element 162 can advance towards the first jaw 154, and in so doing, passes through and cuts or shears the sleeve 112 and extrudable core 111 clamped by the two jaws 154, 156. The resulting configuration of the joining element includes a thicker, cut portion 111b of the core 111 and a thinner, remnant portion 111a that remains associated with the knot 114. The location of where the cutting element 162 cuts the extrudable core 111 can depend on the size of remnant 111a the user would like to leave behind with the knot 114. In the illustrated embodiment, the cutting element 162 cuts the compressed section of the extrudable core 111 approximately in the middle. In other embodiments the cutting element 162 can shear the joining element 110 to cut it proximal to the compression section of the extrudable core 111.

Figure 8D:
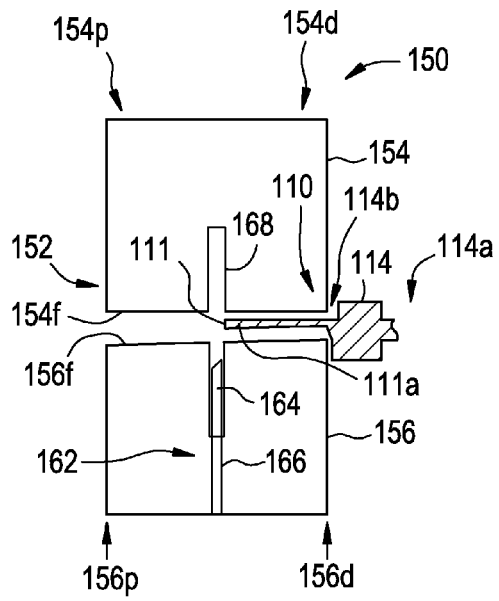
FIG. 8D is a schematic cross-sectional view of the portion of jaws of the instrument of FIG. 8C, the jaws being in an open position and the cutting element being disposed in a first position, a portion of the extrudable core having been removed from the suture.

The resulting configuration is illustrated in FIG. 8D, which provides a remnant 111a extending from the knot 114 and illustrates that the cutting element 162 can be returned to its initial position in the second jaw 156 and the first and second jaws 154, 156 can be opened so that the cut portion 111b of the extrudable core 111 can be removed. The remnant 111a can be at least partially disposed within the sleeve 112. While the remnant 111a can help maintain the integrity of the knot 114, a user may desire to further trim the remnant 111a so that it is not too long. In such an instance, the process can be repeated, or a user can trim the remnant 111a to a desired length using techniques known to those skilled in the art. To the extent techniques known to those skilled in the art are used to further trim the remnant 111a, they do not have the same negative impact as previously described because a large portion of the extrudable core 111 has been removed from the surgical site. Thus, further expansion of the extrudable core 111 is likely to be minimal.

The length of the portion of the extrudable core 111 that is compressed between the jaws 154, 156 can depend on a variety of factors, including but not limited to the length of the overall joining element 110, the desired length of the remnant 111a of the extrudable core 111 after using the device, the tissue or other body parts with which the joining element 110 is associated, and the type of procedure in which the joining element 110 is used. In some exemplary embodiments, a length of the extrudable core 111 prior to being compressed is in the range of about 2 millimeters to about 15 millimeters, and in one exemplary embodiment it is about 4 millimeters. The length of the remnant 111a can likewise depend on a variety of factors, including some of the aforementioned factors. In some exemplary embodiments, a length of the remnant 111a after compression and cutting occurs can be in the range of about 1 millimeters to about 7.5 millimeters, and in one exemplary embodiment it is about 2 millimeters.

The configuration of the extrudable core 111 that results from compression can depend on a variety of factors, including, by way of non-limiting example, the configuration of the jaws 154, 156, the type of material used to form the extrudable core 111, and the length of time that the compressed configuration is maintained before the cutting action occurs. Various jaw configurations and materials for forming the extrudable core 111 are discussed above. In some embodiments, the extrudable core 111 can be compressed by the jaws 154, 156 in the closed configuration for a period of time in the range of about 1 seconds to about 30 seconds, and in one exemplary embodiment the extrudable core 111 can be compressed for a period of less than about 5 seconds.

FIGS. 9A-9D illustrate an alternative embodiment of a system for use in managing a joining element 110'. In this embodiment, the compression element 152' and the cutting element 162' are provided as two separate instruments. Each respective end effector—jaws 154', 156' and cutting blades 164', 165'—can be operated by their own instrument having their own handle portions, triggers, shafts, and other mechanical and electrical components (not shown) used to operate medical instruments as provided for or derivable from the disclosures provided herein or otherwise known to those skilled in the art.

Figure 9A:
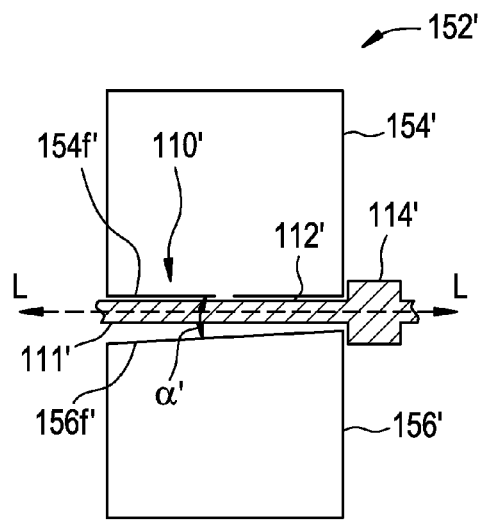
FIG. 9A is a schematic cross-sectional view of one exemplary embodiment of a portion of jaws of an instrument for grasping a suture having an extrudable core, the jaws being in an open position.
Figure 9B:
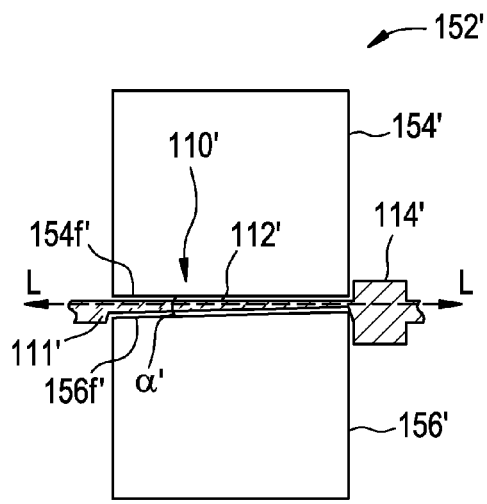
FIG. 9B is a schematic cross-sectional view of the portion of jaws of the instrument of FIG. 9A, the jaws being in a closed position.

As shown in FIG. 9A, the first and second jaws 154', 156' can be configured to engage an outer sleeve 112' and an extrudable core 111' disposed within the sleeve 112' and extending distally from a knot 114' of a joining element 110'. Faces 154f', 156f' of the jaws 154', 156' can once again have an angular configuration such that the face 154f is substantially parallel to a longitudinal axis L extending generally through the jaws 154', 156' and the joining element 110, and the face 156f' is disposed at an angle with respect to the longitudinal axis L to form an angle α' between the first and second faces 154f', 156f'. As illustrated by FIGS. 9A and 9B, the operation of the jaws 154', 156' to compress the extrudable core 111' can be similar to the operation of the jaws 154, 156 of the end effector 150 of FIGS. 8A and 8B. As a result, a thicker portion 111b' of the extrudable core 111' can disposed more distal of the knot 114' than a thinner portion 111a' of the extrudable core 111'.

Figure 9C:
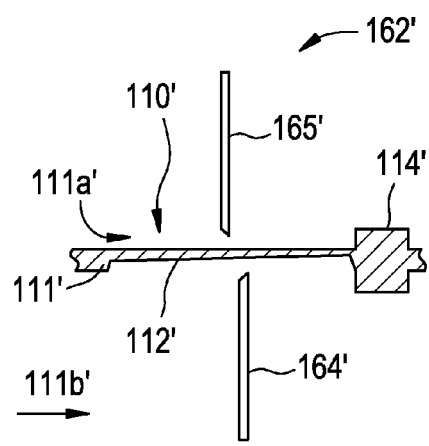
FIG. 9C is a schematic cross-sectional view of one exemplary embodiment of a portion of a cutting instrument for cutting the extrudable core that was grasped by the jaws of FIG. 9B.
Figure 9D:
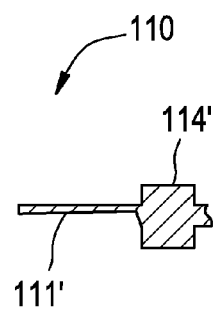
FIG. 9D is a schematic cross-sectional view of a portion of the extrudable core after the cutting instrument of FIG. 9C has cut a portion thereof.

The jaws 154, 156' can then be opened and removed from the surgical site. The extrudable core 111' can be made of a material such that the deformed shape created by the angled jaws 154, 156' can remain even after the jaws 154', 156' are opened, as shown in FIG. 9C. A cutting instrument 162' can then be introduced to cut the extrudable core 111'. Any type of cutting instrument known to those skilled in the art can be used. In the illustrated embodiment, the cutting instrument 162' includes two blades 164, 165, one disposed on either side 111b, 111a' of the extrudable core 111', respectively. As shown, the blades 164, 165' can be slightly offset from each other to aid in achieving a clean cut. After the cut is complete, the knot 114' having a remnant formed from the thinner portion 111a' extending distally therefrom can remain, as shown in FIG. 9D. If further trimming of the remnant 111a' is desired, the instruments can be used again, or further trimming of the remnant 111a' can be performed using techniques known to those skilled in the art.

Other variations of clamping elements or instruments and cutting elements or instruments can be used in conjunction with the disclosures provided for herein. Those skilled in the art will recognize many different ways by which compression and cutting can be achieved in the spirit of the present disclosure.

Figure 10A:
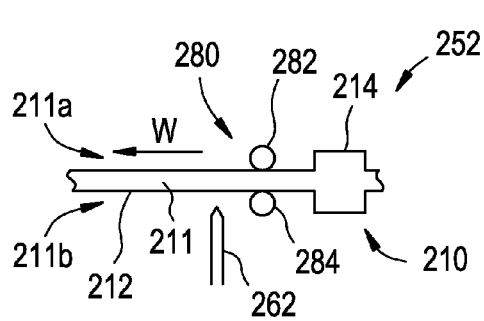
FIG. 10A is a schematic cross-sectional view of one exemplary embodiment of an instrument for grasping and cutting a suture having an extrudable core, the instrument including a pair of opposed rollers for compressing an extrudable core.
Figure 10B:
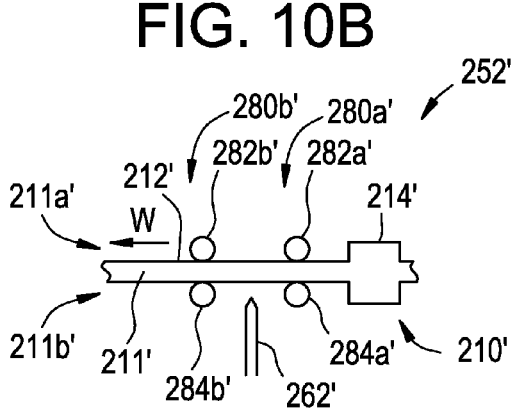
FIG. 10B is a schematic cross-sectional view of another exemplary embodiment of an instrument for grasping and cutting a suture having an extrudable core, the instrument including two pairs of opposed rollers for compressing an extrudable core.

For example, an extrudable core can be compressed using other techniques. In one non-limiting example, illustrated in FIGS. 10A and 10B, an instrument 252 for applying peristaltic compression can be used to drive a portion of an extrudable core 211 disposed in an outer sleeve 212 of a joining element 210 away from a knot 214. More particularly, one or more pairs of opposed rollers 280 can be disposed on opposite sides 211a, 211b of the extrudable core 211, similar to the location of the first and second jaws in previously described embodiments. In FIG. 10A, a first roller 282 is located on the first side 211a and a second roller 284 is located on the second side 211b. The rollers 282, 284 can then be actuated to be pinched towards each other and advanced distally, away from the knot 214 in the direction W, to push the extrudable core 211 away from the knot 214. The core 211 can be advanced with respect to the outer sleeve 212 such that at least a portion of the outer sleeve 212 has a partially filled or unfilled volume. The amount of pressure applied by the rollers 282, 284 to the extrudable core 211 can be controlled as desired to result in desired compressed configurations. Alternatively, the sleeve 212 and extrudable core 211 can be grasped with rounded grips and pulled, thereby extruding at least a portion of the core. In FIG. 10B, a peristaltic compression instrument 252' can include two pairs of rollers 280a', 280b' with a first roller 282a' and third roller 282b' located on a first side 211a' of an extrudable core 211' of a joining element 210', and opposed second and fourth rollers 284a', 284b' located on a second side 211b' of the extrudable core 211. The rollers can be actuated and advanced in a manner similar to the rollers of FIG. 10A, and thus can be configured to distally advance the extrudable core 211' in a direction W', away from the knot 214'. The core 211' can be advanced with respect to the outer sleeve 212' such that at least a portion of the outer sleeve 212' has a partially filled or unfilled volume.

The rollers 280, 280' can have many sizes, but in some embodiments radii thereof can be kept relatively small so that the rollers can keep the remaining remnant portion close to the knot. The overall size of the rollers 280, 280' can depend, at least in part, on the sizes, shapes, and configurations of the other components with which the rollers are used and the type of procedure in which they are used. A cutting instrument 262, 262' can be incorporated with the rollers 280, 280' to cut the compressed core 211, 211' at a desired location. While the cutting instrument can be disposed at a variety of locations, in the embodiment of FIG. 10A, the cutting instrument 262 is disposed at a desired length distal of the knot 214, and the cutting instrument 262 can be actuated after the rollers 280 advance distally past the cutting instrument 262. Alternatively, as shown in FIG. 10B, the cutting instrument 262' can be disposed between the pairs of rollers 280a', 280b'. In other instances the cutting instrument can be disposed after a last pair of rollers. Still further, a separate cutting instrument, separate from the peristaltic compression instrument, can also be used.

Figure 10C:
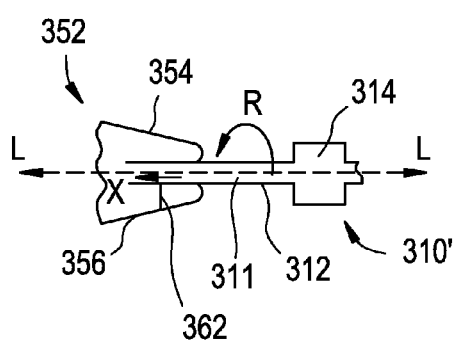
FIG. 10C is a schematic cross-sectional view of one exemplary embodiment of an instrument for grasping and cutting a suture having an extrudable core, the instrument being configured to apply an axial torsion to the extrudable core.

By way of further non-limiting example, axial torsion can be use to drive a portion of the extrudable core away from the knot. As shown in FIG. 10C, an instrument 352 can have jaws 354, 356 that can be disposed around a portion of an extrudable core 311 disposed in an outer sleeve 312 of a joining element 310 that extends distally from a knot 314. The jaws 354, 356 can engage the sleeve 312, and thus the core 311, and then twist the sleeve 312 and core 311 in a direction R around a longitudinal axis L extending substantially through the core 311 to cause the core 311 to spin and compress away from the knot 314. As more axial torsion is applied to the core 311, the portion of the core 311 closest to the knot can become thinner as more of the core 311 moves away from the knot 314, in a direction X. The torsion can be applied to such a degree that it finally causes the core 311 to break into two pieces, leaving a remnant behind. A portion of the sleeve 312 can be partially filled with the remnant of the core 311 or unfilled. Alternatively, a cutting element 362 can be incorporated into the axial torsion instrument 352, as shown in FIG. 10C, or a separate cutting instrument can be provided. The cutting instrument 352 can operate in a manner similar to the disclosures provided for herein relating to various cutting elements and instruments.

Figure 10D:
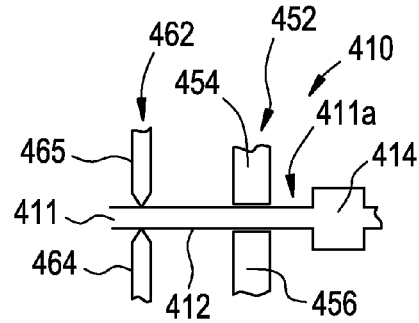
FIG. 10D is a schematic cross-sectional view of one exemplary embodiment of an instrument for grasping and cutting a suture having an extrudable core, the instrument having a compression element disposed distal of a cutting element.
Figure 10E:
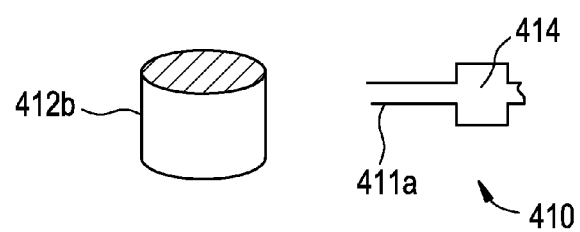
FIG. 10E is a schematic illustration of the suture of FIG. 10D with a portion of an outer sleeve of the suture being detached from a portion of the extrudable core.

By way of still a further non-limiting example, a compression portion 452 and a cutting portion 462 can be separated and more nuanced, as shown in FIG. 10D. For example, in some embodiments the compression instrument 452, as shown jaws 454, 456, can be configured to pinch an extrudable core 411 disposed in an outer sleeve 412 of a joining element 410 and cause it to fracture, while the cutting instrument 462, as shown cutting blades 464, 465, can be disposed more distal to a knot 414 associated with the joining element 410 than the compression instrument 452 is. In such an embodiment, the cutting instrument 462 can be designed to only cut through the outer sleeve 412 of the joining element 410, as opposed to the entire joining element 410, thereby leaving the fractured core 411 intact. Subsequently, the length of the fractured core 411 can be removed from a remnant portion 411a of the joining element 410, through the portion of the out sleeve 412 that was cut. As a result, a remnant core 411 can remain between the knot 414 and a location proximate to the compression instrument 452, and a substantially empty sleeve 412 can remain between the location proximate to the compression instrument 452 and a location proximate to the cutting instrument 462. In embodiments in which the outer sleeve 412 is a continuous filament, then its surface can be scored with a blade such that the blade cuts through the outer sleeve 412 while keeping the core 411 intact. As a result, the continuous filament can be removed, leaving it as a hollow, individual piece 412b, and the remnant portion 411a of the extrudable core 411 can be exposed due to the removal of the continuous filament 412b, as illustrated in FIG. 10E. The remnant portion 411a can be cut or otherwise trimmed using techniques provided for herein or otherwise known to those skilled in the art.

Figure 11A:
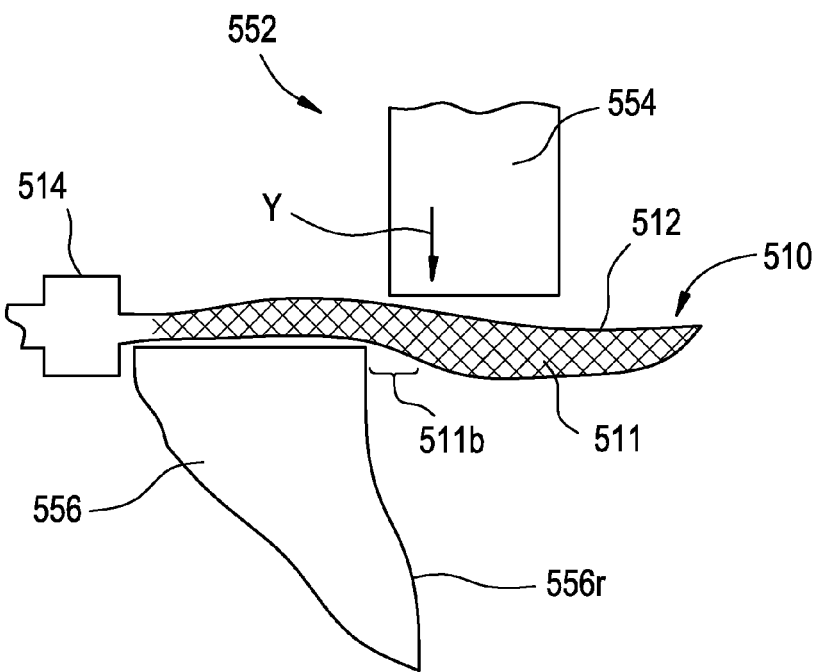
FIG. 11A is a schematic cross-sectional view of another exemplary of a portion of jaws of an instrument for grasping and cutting a suture having an extrudable core, the jaws being in a first position.
Figure 11B:
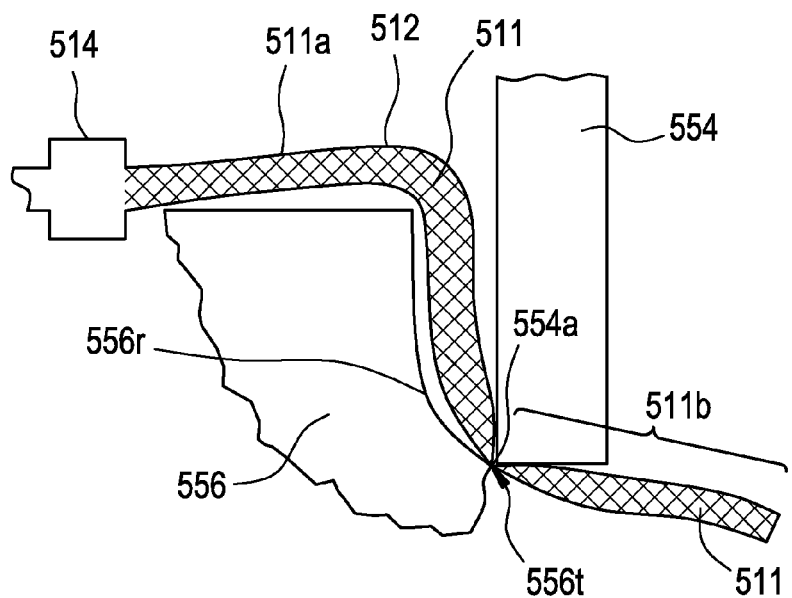
FIG. 11B is a schematic cross-sectional view of the portion of jaws of the instrument of FIG. 11A, the jaws being in a second position.

FIGS. 11A and 11B illustrate an additional non-limiting example of a configuration for compressing and cutting a joining element 510. As shown in FIG. 11A, first and second jaws 554, 556 of a compression element 552 can be substantially rigid and slightly offset from one another, with the first jaw 554 being more distal from a knot 514 formed as part of the joining element 510 than the second jaw 556. As the first jaw 554 is advanced in a downward direction Y, towards the second jaw 556, an extrudable core 511 disposed in an outer sleeve 512 of the joining element 510 and disposed between the first and second jaws 554, 556 can be pinched between the two jaws 554, 556, resulting in that portion squeezing out past a location at which the jaws 554, 556 cut the joining element 510, as shown in FIG. 11B. A section of the core 511 disposed between the two jaws 554, 556 can break due to the force, and a portion of the core section 511b can be squeezed distally out ahead of the first jaw 554 as the first jaw 554 continues its advancement in the direction Y. As shown, a surface of the second jaw 556 can have a ramped portion 556r that helps push the core section 511b out ahead of the first jaw 554. A terminal end 556t of the ramped portion 556r can be located just proximal of an end 554a of the first jaw 554 such that the joining element 510 can be pinched between the first jaw 554 and the terminal end 556t to separate the core portion 511b squeezed out ahead of the first jaw 554 from a remaining portion 511a of the core 511. The jaws 554, 556 can then be effective to cut the jacket 512, and thus the joining element 510 since the extrudable core 511 has already been squeezed out ahead, such that a remaining portion 511a of the extrudable core 511 can be a remnant portion 511a. The remnant portion 511a can then be trimmed as desired, similar to previously described embodiments. A person skilled in the art will recognize that the geometries of the first and second jaws 554, 556 can be adapted to create other desired effects. For example, the offset between the two jaws 554, 556 can be optimally graded across a wide region such that the shearing motion can become increasingly restrictive, thereby effectively squeezing out the extrudable core 511 from the jacket 512 just prior to the jacket 512 finally being cut.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   implanting a suture within a patient, the suture having an outer sleeve and an extrudable core disposed within the outer sleeve, and the suture further having a knot formed therein portions of the extrudable core being disposed on opposed lateral sides of the knot;
   clamping the extrudable core disposed on one side of the knot by engaging a first portion of the extrudable core disposed adjacent to the knot with a first jaw and a second jaw when the first jaw is moved with respect to the second jaw as part of a closure motion prior to engaging a second portion of the extrudable core disposed further from the knot than the first portion with the first and second jaws during the same closure motion of the first and second jaws such that the extrudable core is compressed, thereby causing the extrudable core to advance a distance away from the knot; and
   cutting a portion of the extrudable core that was advanced the distance away from the knot by the clamping step such that the cut portion is no longer associated with a remaining portion of the extrudable core.

2. The method of 1, wherein the steps of clamping and cutting are performed by a single instrument having a housing with both the first and second jaws and a cutting element associated therewith.

3. The method of 2, wherein the instrument comprises a trigger, the method further comprising:
   advancing the trigger a first distance to clamp and advance the extrudable core; and
   advancing the trigger a second distance, which extends further than an end point of the first distance, to cut a portion of the extrudable core that was advanced during clamping.

4. The method of 2, wherein the instrument comprises a trigger, the method further comprising:
advancing the trigger a first distance to clamp and advance the extrudable core; and
subsequently, operating the trigger to actuate a gear that initiates cutting a portion of the extrudable core that was advanced during clamping.

5. The method of 1, wherein the steps of clamping and cutting are performed by two separate instruments, each operable independently from the other.

6. The method of claim 1, wherein a face of the second jaw is angularly disposed with respect to a face of the first jaw when the jaws are in a closed position, the closed position being a position at which the jaws engage the first and second portion of the extrudable core to cause the extrudable core to advance the distance away from, the knot.

7. The method of claim 6, wherein an angle formed between the face of the first jaw and the face of the second jaw in the closed position is in the range of about 0.5 degrees to about 20 degrees.

8. A surgical method, comprising:
implanting a suture within a patient, the suture having an outer sleeve and an extrudable core disposed within the outer sleeve, the suture further having a knot formed therein and portions of the extrudable core disposed on opposed lateral sides of the knot;
actuating an instrument having a first jaw and a second jaw to perform a closure stroke such that a first portion of one of the first and second jaws engages a first segment of the extrudable core proximate to the knot prior to a second portion of the one of the first and second jaws that is more distal with respect to the knot than the first portion engages a second segment, of the extrudable core that is more distal with respect to the knot than the first segment during the closure stroke, thereby causing the extrudable core to advance a distance away from the knot; and
cutting a portion of the extrudable core that was advanced, the distance away from the knot by the actuating step such that the cut portion is no longer associated with a remaining portion of the extrudable core.

9. The method of claim 8, wherein the steps of actuating and cutting are both performed by the instrument, the instrument having a cutting element disposed within one of the first and second jaws.

10. The method of 9, wherein the instrument comprises a trigger, the method further comprising:
advancing the trigger a first distance to perform the actuating step and advance the extendable core; and
advancing the trigger a second distance, which extends further than an end point of the first distance, to cut the portion of the extrudable core.

11. The method of claim 9, wherein the instrument comprises a trigger, the method further comprising:
advancing the trigger a first distance to perform the actuating step and advance the extrudable core; and
subsequently, operating the trigger to actuate a gear that initiates cutting the portion of the extrudable core.

12. The method of claim 8, wherein the cutting step is performed by a second instrument, separate from the instrument that is actuated to advance the extrudable core, with the second instrument and the instrument that is actuated to advance the extrudable core being operably independent from each other.

13. The method of claim 8, wherein a face of the second jaw is angularly disposed with respect to a face of the first jaw when the jaws are in a closed position, the closed position being a position at which the jaws engage the extrudable core to advance the extrudable core the distance away from the knot.

14. The method of claim 9, wherein an angle formed between the face of the first jaw and the face of the second jaw in the closed position is in the range of about 0.5 degrees to about 20 degrees.

* * * * *